(12) United States Patent  
Neer

(10) Patent No.: US 8,657,787 B2  
(45) Date of Patent: Feb. 25, 2014

(54) INJECTOR HAVING LOW INPUT POWER

(75) Inventor: Charles S. Neer, Cincinnati, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 177 days.

(21) Appl. No.: 12/444,162

(22) PCT Filed: Sep. 25, 2007

(86) PCT No.: PCT/US2007/020694  
§ 371 (c)(1),  
(2), (4) Date: Apr. 3, 2009

(87) PCT Pub. No.: WO2008/045203  
PCT Pub. Date: Apr. 17, 2008

(65) Prior Publication Data  
US 2010/0030153 A1 Feb. 4, 2010

Related U.S. Application Data

(60) Provisional application No. 60/850,892, filed on Oct. 11, 2006.

(51) Int. Cl.  
*A61M 5/20* (2006.01)

(52) U.S. Cl.  
USPC .......................................................... 604/156

(58) Field of Classification Search  
USPC .................................................. 604/154, 156  
See application file for complete search history.

(56) References Cited

U.S. PATENT DOCUMENTS

| | | |
|---|---|---|
| 4,408,607 A | 10/1983 | Maurer |
| 4,685,903 A | 8/1987 | Cable et al. |
| 4,925,443 A | 5/1990 | Heilman et al. |
| 5,040,537 A | 8/1991 | Katakura |
| 5,494,036 A | 2/1996 | Uber, III et al. |
| 5,591,217 A | 1/1997 | Barreras |
| 5,733,313 A | 3/1998 | Barreras, Sr. et al. |
| 6,259,951 B1 | 7/2001 | Kuzma et al. |
| 6,595,756 B2 | 7/2003 | Gray et al. |
| 6,650,091 B1 | 11/2003 | Shiue et al. |
| 6,669,663 B1 | 12/2003 | Thompson |
| 6,753,673 B2 | 6/2004 | Shiue et al. |
| 6,845,267 B2 | 1/2005 | Harrison et al. |
| 6,853,858 B2 | 2/2005 | Shalev |
| 6,922,590 B1 | 7/2005 | Whitehurst |
| 6,939,323 B2 | 9/2005 | Angel et al. |
| 7,224,143 B2 | 5/2007 | Liscio et al. |
| 7,414,382 B2 | 8/2008 | Liscio et al. |
| 2004/0155628 A1* | 8/2004 | Liscio et al. .................. 320/127 |
| 2004/0264085 A1* | 12/2004 | Thrap ............................. 361/90 |
| 2008/0309295 A1 | 12/2008 | Kotz et al. |

FOREIGN PATENT DOCUMENTS

| | | |
|---|---|---|
| GB | 2 423 199 | 8/2006 |
| JP | 2004180931 | 7/2004 |
| JP | 2004-297992 A | 10/2004 |
| WO | WO 02/091008 | 11/2002 |

(Continued)

*Primary Examiner* — Jason Flick  
*Assistant Examiner* — Rebecca E Eisenberg

(57) ABSTRACT

A powered injector that stores energy at a low rate when not in use and delivers energy at a high rate during injection. Energy may be stored in a highly responsive energy storage device, such as a capacitor, for rapid delivery of power to the injector motor. In certain embodiments, wires connecting the powered injector to a power supply may be relatively small and inexpensive because the current and voltage loads placed on the wires are relatively low.

20 Claims, 8 Drawing Sheets

(56) References Cited

FOREIGN PATENT DOCUMENTS

| WO | 03039635 | 5/2003 |
| WO | 2006032621 | 3/2006 |
| WO | 2006/085098 | 8/2006 |

* cited by examiner

INJECTOR HAVING LOW INPUT POWER

RELATED APPLICATIONS

This application claims priority to U.S. provisional application Ser. No. 60/850,892 filed on 11 Oct. 2006 and entitled INJECTOR HAVING LOW INPUT POWER.

FIELD OF THE INVENTION

The invention relates generally to powered injectors for injecting medical fluid and, more specifically, to powered injectors that have a low input power level relative to an output power level thereof.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Generally, a powered injector is used to inject medical fluid, such as a pharmaceutical or a contrast agent, into a patient. Typically, a motor in the powered injector is utilized to drive a plunger of a syringe forward to inject medical fluid therefrom. A power supply generally provides energy to the motor. Frequently, the power supply is remote from the powered injector to reduce the likelihood of electromagnetic emissions from the power supply interfering with other medical equipment, such as medical imaging equipment.

Unfortunately, supplying power to the motor often presents design challenges to manufacturers of powered injectors. The motor often consumes energy at a high rate while moving the plunger of the syringe. Wires between the power supply and the motor are typically utilized to carry large currents and/or voltages to supply sufficient power to the motor. Wires having sufficient capacity to deliver this power are often expensive. This expense may be attributed to the thickness of the wires and/or high-cost materials utilized to construct such wires. For instance, wires suitable for high voltages often include expensive insulation. Further, because the power supply is often remote from the powered injector, the wires connecting the two are often very long. Thus, wires for delivering high power to the powered injector may add significant cost to a design.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In certain aspects, the present invention generally relates to a powered injector that gradually stores energy at a low rate (e.g., at low power) when not in use and then quickly delivers energy at a high rate (e.g., at high power) during operation (e.g., during an injection procedure). Energy may be stored in a highly responsive energy storage device, such as a capacitor, for rapid delivery of power to the motor. In certain embodiments, wires connecting the powered injector to a power supply may be small and inexpensive (relative to conventional wire interconnections between injectors and power supplies) because the current and voltage loads placed on the wires are low (again, relative to conventional wire interconnections between injectors and power supplies).

A first aspect of the invention is directed to a powered injector that includes an energy storage device having a power input and a power output, a motor coupled to the power output of the energy storage device, and a ram that is coupled to the motor and that has a syringe plunger interface. The current carrying capacity of the power output of the energy storage device is greater (and in some cases, substantially greater) than the current carrying capacity of the power input of the energy storage device.

A second aspect of the invention is directed to an electric injector for use with a syringe having medical fluid (e.g., contrast media, radiopharmaceutical, saline, etc.) therein. This injector includes a plurality of supercapacitors coupled to one another in series, a motor coupled in parallel to the plurality of supercapacitors, and a syringe interface coupled to the motor.

Yet a third aspect of the invention is directed to a method of operation for a medical fluid injector. In this method, input power is received by the injector from a power supply at an input wattage. The input power is stored by the injector. Subsequently, discharge power is output by the injector at an output wattage that is at least twice as great as the input wattage.

Various refinements exist of the features noted above in relation to the various exemplary aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

These and other features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a", "an", "the", and "said" are intended to mean that there are one or more of the elements. The terms "comprising", "including", and "having" are intended to be inclusive and mean that there may be additional elements other than the listed elements. Moreover, the use of "top", "bottom", "above", "below" and variations of these terms is made for convenience, but does not require any particular orientation of the components. Further, as used herein, the terms "high power" and "low power" refer to power levels that are high or low relative to one another, rather than power above or below an absolute threshold level. The term "coupled" refers to a condition in which two or more objects are in direct contact or are interconnected (i.e., either directly or indirectly connected). The phrase "fluidly coupled" refers to a condition in which two or more objects are coupled in a manner such that fluid can flow from one object to another.

Figure 1:
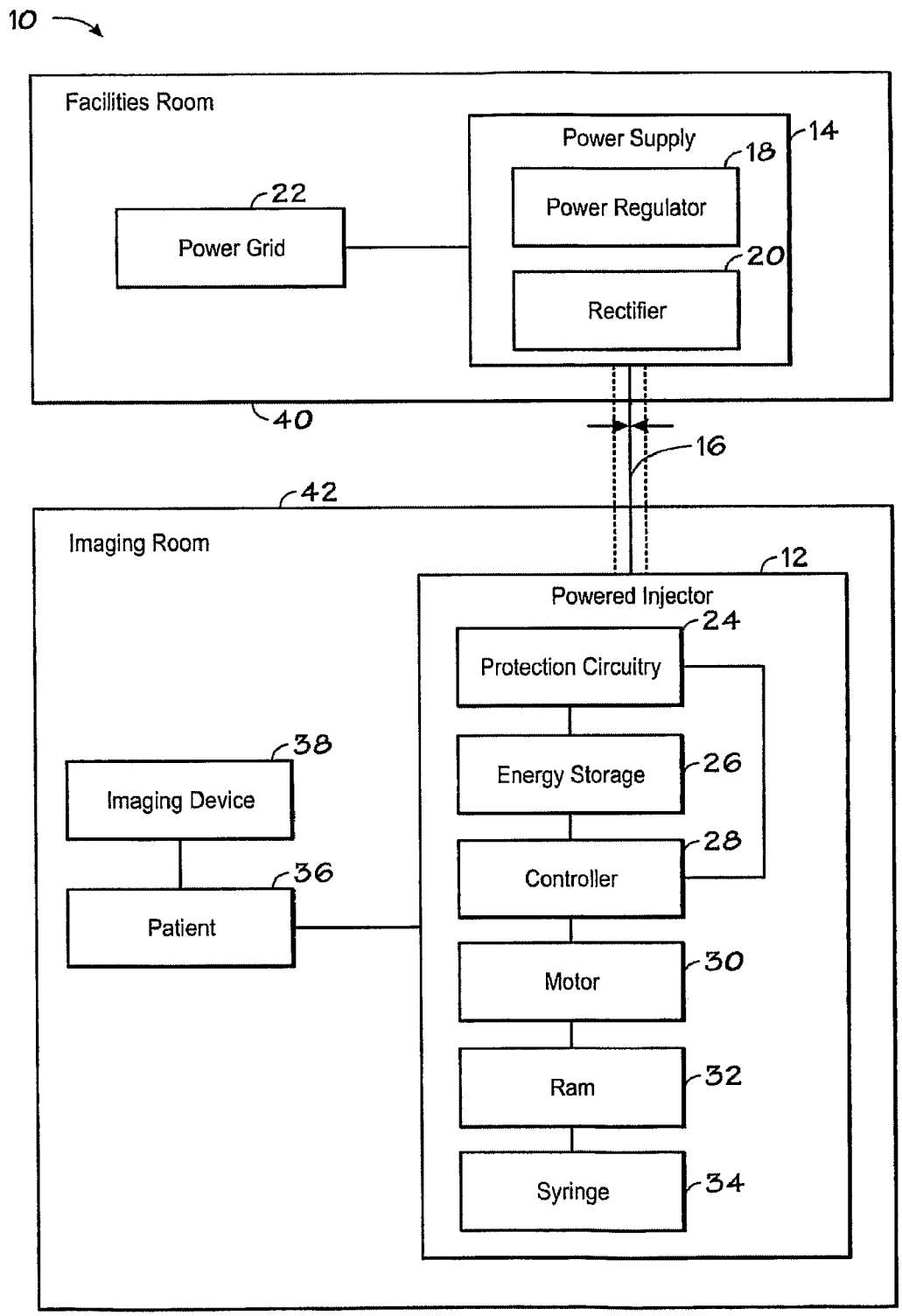
FIG. 1 is a diagram of an exemplary injection system.

FIG. 1 illustrates an exemplary injection system 10 having a powered injector 12 coupled to a power supply 14 by a power cable 16. Advantageously, certain embodiments may include a relatively low cost power cable 16. As explained further below, the exemplary powered injector 12 of FIG. 1 stores energy delivered at a relatively low input power level, thereby potentially reducing the peak power carried by the power cable 16. Subsequently, the powered injector 12 uses the stored energy at a high output power level during an injection. Certain embodiments may include relatively small, inexpensive, and/or long cables that carry power to the powered injector. Some of these embodiments may facilitate remote placement of the powered injector relative to a power source. Prior to addressing the powered injector 12 in detail, features of the power supply 14 are explained.

The power supply 14 of FIG. 1 includes a power regulator 18 and a rectifier 20. The power regulator 18 may include or be referred to as a current limiter, a transformer, or a power source controller, and the rectifier 20 may be referred to or include an alternating current (AC) to direct current (DC) converter. The power regulator 18 may have an AC power regulator, such as a silicon controlled rectifier and control circuitry, and/or a DC power regulator, such as a switching regulator, or a current or voltage divider. In certain embodiments, the rectifier 20 may have a low-pass filter and half-wave rectifier or a full-wave rectifier. Further, some embodiments may include a band-pass filter to reduce the likelihood of high and low frequency electromagnetic signals reaching the powered injector 12. The power supply 14 may couple to a source of power, such as a power grid 22.

In the illustrated embodiment, the powered injector 12 includes protection circuitry 24, an energy storage device 26, a controller 28, a motor 30, a ram 32, and a syringe 34. The protection circuitry 24 may include devices adapted to limit the magnitude of currents flowing into the energy storage device 26, such as a fuse, a circuit breaker, or a current divider.

The energy storage device 26 may include or be referred to as a local energy source, a local energy storage, an on-board power supply, and/or an integrated power source. The energy storage device 26 may include a variety of devices configured to receive, store, and supply energy. For instance, the energy storage device 26 may include a capacitor, such as a supercapacitor (e.g., available from Maxwell Technologies of San Diego, Calif.). As used herein, the term "supercapacitor" refers to a capacitor having a gravimetric energy density greater than 0.4 Joules per gram. In some embodiments, the energy storage device 26 may include a capacitor exhibiting a capacitance greater than or equal to 1 farad, 10 farads, 30 farads, 100 farads, 200 farads, 300 farads, 350 farads, 500 farads, 1000 farads, 1500 farads, 2000 farads, or even more. Alternatively or additionally, the energy storage device 26 may include a battery, such as a lead-acid battery, a lithium ion battery, a lithium ion polymer battery, a nickel-iron battery, a nickel metal hydride battery, a nickel cadmium battery, a sodium metal chloride battery, or a nickel-zinc battery.

The controller 28 may include circuitry and/or code adapted to control a flow of energy from the energy storage device 26 to the motor 30 of the injector 12. In some embodiments, the controller 28 may include logic circuitry, such as a central processor, a digital signal processor, an application specific integrated circuit, a microcontroller, or the like. The controller 28 may be equipped with a switch capable of preventing or modulating the flow of current from the energy storage device 26 in response to signals from the logic circuitry. For instance, certain embodiments may include an integrated gate bi-polar transistor (IGBT), a bipolar junction transistor, a metal oxide semiconductor field effect transistor (MOSFET), a mechanical relay, a solenoid, or a solid state relay. The controller 28 may include or couple to a user interface through which a user may signal the controller 28 to initiate an injection. For example, the user interface may include a graphical user interface.

In the illustrated embodiment, the motor 30 and ram 32 may include a variety of devices for converting electrical energy into a desired form of mechanical energy. For instance, the motor may include various types of electric motors, such as a stepper motor, a brush DC motor, a brushless DC motor, a linear motor, or a piezoelectric drive. The ram 32 may include a syringe interface and a transmission. The syringe interface may include or be referred to as a plunger interface, a pushing surface, and/or a pressure applicator. The transmission may include or be referred to as a drive, a gear-box, a rotation-to-linear motion transmission, and/or a motor-syringe mechanical interface.

The syringe 34 of the illustrated embodiment may include a plunger, a barrel, and medical fluid disposed within the barrel. The medical fluid in the syringe may be any appropriate medical fluid such as, but not limited to, saline, a contrast agent, a pharmaceutical, a radiopharmaceutical, or a combination thereof. In the current embodiment, the plunger is disposed within the barrel, and together, the plunger and barrel house the medical fluid. A backside of the plunger may include a surface and/or structure designed/configured to interface with the syringe interface of the ram 32.

The protection circuitry 24 is shown as being electrically disposed (i.e., positioned with reference to a flow of electrons) between the energy storage device 26 and the power supply 14, and the controller 28 is shown as being electrically disposed between the energy storage device 26 and the motor 30. The protection circuitry 24 may serially couple to the power cable 16 and the energy storage device 26. The energy storage device 26 may be serially coupled to the motor 30 via the controller 28. The controller 28 may also couple to the protection circuitry 24. The motor 30 may mechanically connect to a transmission of the ram 32, and the ram 32 may be designed to interface with (e.g., mechanically couple to) the plunger of the syringe 34 via the syringe interface.

The powered injector 12 of FIG. 1 may be fluidly coupled to a patient 36 or other organism via a conduit and a hollow, hypodermic needle. In certain embodiments, an imaging device 38 (may be utilized to image the patient 36 during and/or after injection of medical fluid into the patient 36. The imaging device 38 may refer to or include a variety of imaging systems such as a projection radiography system (e.g., an x-ray system), a fluoroscopy system, a tomography system (e.g., a computed axial tomography system), a magnetic resonance imaging (MRI) system, and/or an ultrasound system.

In some embodiments, the powered injector 12, the patient 36, and the imaging device 38 may be remote from the power supply 14. For instance, in the injection system 10 of FIG. 1, they are in separate rooms, with the power supply 14 disposed in a facilities room 40 and the other components in an imaging room 42. In certain embodiments, to extend between these rooms 40, 42, the power cable 16 may be longer than 1 meter, 2 meters, 3 meters, 6 meters, 10 meters, 20, meters, 50 meters, or more. The imaging room 42 may include various forms of shielding, such as electromagnetic shielding, to isolate the imaging device 38 from some sources of interference. In some embodiments, the imaging room 42 may be generally free of ferrous materials that might be attracted to magnets and/or cause image artifacts in an MRI machine. Advantageously, by positioning the power supply 14 remote from the powered injector 12, the injection system 10 may tend to reduce interference with the imaging device 38 from the power supply 14.

Figure 2:
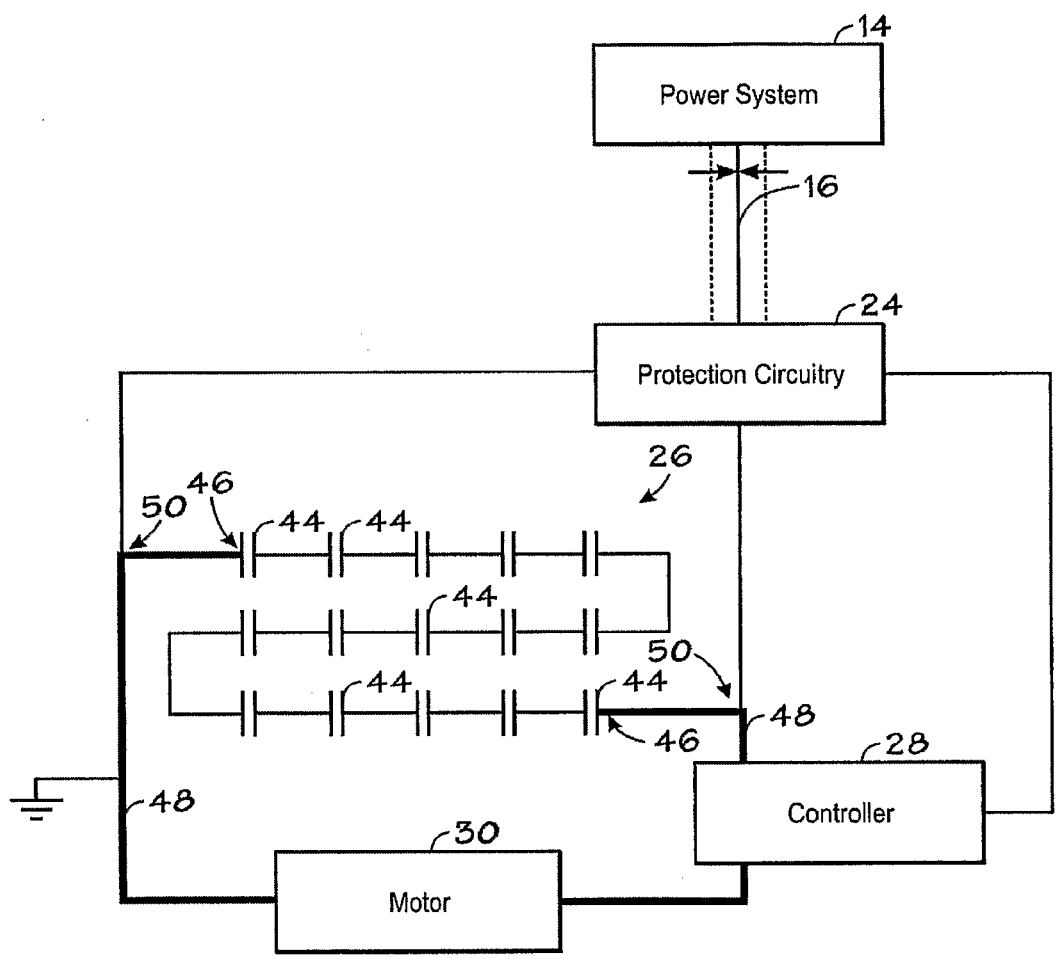
FIG. 2 is a diagram of a powered injector in the injection system of FIG. 1.

Turning to FIG. 2, the exemplary energy storage device 26 is depicted in greater detail. The illustrated energy storage device 26 includes a bank of supercapacitors 44 coupled in series. The present embodiment includes fifteen supercapacitors 44, but other embodiments may include any appropriate and/or desired number of supercapacitors. For instance, some embodiments include more than one supercapacitor, more than two, more than three, more than four, more than five, more than ten, more than twenty, more than fifty, or even more than one hundred supercapacitors. The serially connected supercapacitors 44, when fully charged, output a current of approximately 40 amps at an aggregate voltage of approximately 38 volts. In other words, the energy storage device 26 outputs approximately 1500 watts of power. Other embodiments of the energy storage device 26 provide output of other appropriate wattages. For instance, in some embodiments, the energy storage device 26 may output more than 500 watts, more than 700 watts, more than 1000 watts, more than 1200 watts, more than 1500 watts, more than 1700 watts, more than 2000 watts, more than 2500 watts, or even more.

To carry this power, in some embodiments, a power output 46 of the energy storage device 26 may couple to a high current (or voltage) capacity conductor 48. In certain embodiments, the conductor 48 may be a low gauge wire of relatively short length (e.g., a 10 to 14 AWG gauge wire of less than about two feet in length). That is, the conductor 48 may have a conductive portion with a cross-sectional area greater than or equal to about $3.3 \times 10^{-3}$ square inch, greater than or equal to about $5.2 \times 10^{-3}$ square inch, greater than or equal to about $8.2 \times 10^{-3}$ square inch, or greater than or equal to about $1.3 \times 10^{-2}$ square inch.

In contrast, the wires connecting the energy storage device 26 and the power system 14, including the power cable 16, may have a much lower current carrying capacity than the conductor 48. For example, the power cable 16 may be embodied by a 25-pin cable with a D-shell pin connector and 22 gauge wires (wire having a diameter of about $2.5 \times 10^{-2}$ inch). In certain embodiments, the power cable 16 may include or consists essentially of a wire or wires having a conductive portion with a cross-sectional area less than or equal to about $2.6 \times 10^{-3}$ square inch, less than or equal to about $1.2 \times 10^{-3}$ square inch, less than or equal to about $8.0 \times 10^{-4}$ square inch, less than or equal to about $5.0 \times 10^{-4}$ square inch, less than or equal to about $2.5 \times 10^{-4}$ square inch, or less than or equal to about $1.6 \times 10^{-4}$ square inch. The power cable 16 may couple to a power input 50 of the energy storage device 16. In some embodiments, five wires of the cable 16 may carry a ground voltage and five wires may conduct current driven by a DC voltage less than 42 volts through the power input 50. Advantageously, the power cable 16 and electronics in the power supply 14 may be less expensive than components adapted to deliver 1500 watts of power the entire distance from the power supply 14 to the motor 30.

Figure 3:
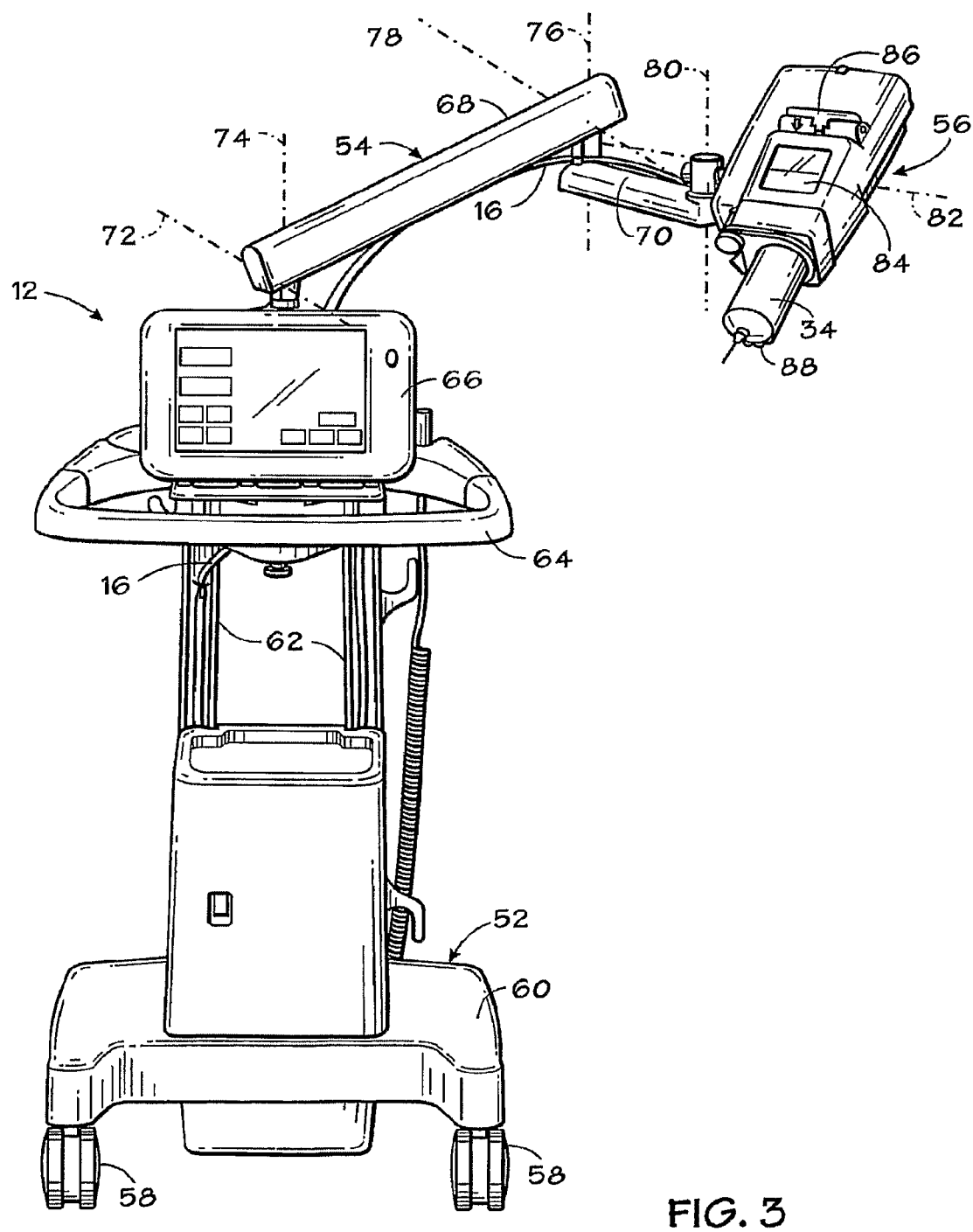
FIG. 3 is an elevation view of the powered injector of FIG. 1.

FIG. 3 is an elevation view the exemplary powered injector 12. As illustrated by FIG. 3, the powered injector 12 includes a stand assembly 52, a support arm 54, and a power head 56. The illustrated stand assembly 52 includes four sets of wheels 58, a chassis 60, vertical supports 62, a handle 64, and a display 66. The vertical supports 62 may elevate the handle 64, display 66, and support arm 54 above the chassis 60, and, in certain embodiments, it may have a recessed portion through which the power cable 16 is routed. The display 66 may include a liquid crystal display, a cathode ray tube display, an organic light emitting diode display, a surface emission display, or other appropriate display, and it may be coupled to the controller 28.

The support arm 54 of the injector 12 shown in FIG. 3 includes multi-axis articulating members 68, 70. The illustrated articulating member 68 has two degrees of freedom relative to the chassis 60 due to two perpendicular axes of rotation 72, 74. Similarly, the exemplary articulating member 70 has two degrees of freedom relative to the articulating member 68 by virtue of two perpendicular axes of rotation 76, 78. The power cable 16 is shown as being routed along the articulating members 68, 70 to the power head 56.

The power head 56 of FIG. 3 couples to the articulating member 70 via a joint that provides two degrees of freedom relative to the articulating member 70. As a result, in the present embodiment, the power head 56 may rotate about axes 80, 82. In total, the illustrated power head 56 has six degrees of freedom relative to the chassis 60. Other embodiments may include more or fewer degrees of freedom.

The power head 56 includes a display 84, a fluid control bar 86, and an air detector 88. The fluid control bar 86 facilitates manual manipulation of the plunger in the syringe 34, and the air detector 88 signals the controller 28 when air is detected leaving the syringe 34.

In the present embodiment, the power head 56 houses the protection circuitry 24, the energy storage device 26, the controller 28, the motor 30, the ram 32, and a portion of the syringe 34. In other embodiments, a number of these components or a portion of these components may be distributed elsewhere on the powered injector 12 or elsewhere in the injecting system 10 (FIG. 1).

Figure 4:
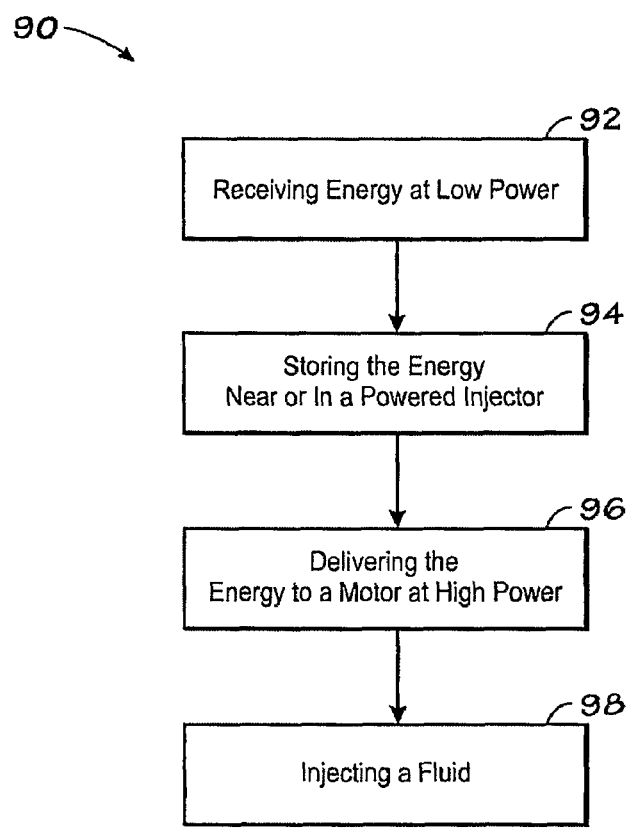
FIG. 4 is a flow chart depicting an exemplary injection process.

The powered injector 12 may operate according to an exemplary injection process 90 depicted by FIG. 4. The energy storage device 26 receives energy at low power, as depicted by block 92. In some embodiments, the energy storage device 26 may receive this energy via the power cable 16 from the power supply 14. During this step 92, a charging current may flow through the power input 50 of the energy storage device 26. The charging current may be delivered at low power, such as less than 500 watts, less than 400 watts, less than 300 watts, less than 200 watts, less than 100 watts, less than 50 watts, less than 10 watts, or even less. As energy is delivered by the power cable 16, it may be stored in the energy storage device 26, as depicted by block 94. For example, a charge may build on plates of the capacitors 44. In some embodiments, the energy storage device 26 may be charged through induction (e.g., in cordless embodiments).

Next in the exemplary injection process 90, the energy storage device 26 delivers energy to the motor 30 at high power, as depicted by block 96. For example, the controller 28 may close a current path through the conductor 48 by energizing a gate of a solid state switching device, and the capacitors 44 may discharge through the power output 46 and the conductor 48. In certain embodiments, the energy storage device 26 may deliver energy at a rate of more than 700 watts, more than 800 watts, more than 1000 watts, more than 1200 watts, more than 1400 watts, more than 1500 watts, more than 1700 watts, more than 2000 watts, more than 3000 watts, more than 5000 watts, or more.

As depicted by block 98, the injection process 90 includes injection of a medical fluid. In the powered injector 12 of FIGS. 1-3, current from the energy storage device 26 powers the motor 30, and the motor 30 drives the ram 32. The ram 32, in turn, pushes a plunger of the syringe through the barrel of the syringe 34, and pushes the medical fluid out of the syringe and into the patient 36. The medical fluid may include any appropriate medical fluid such as a contrast agent, a pharmaceutical, a radiopharmaceutical, saline, or a combination thereof.

Figure 5:
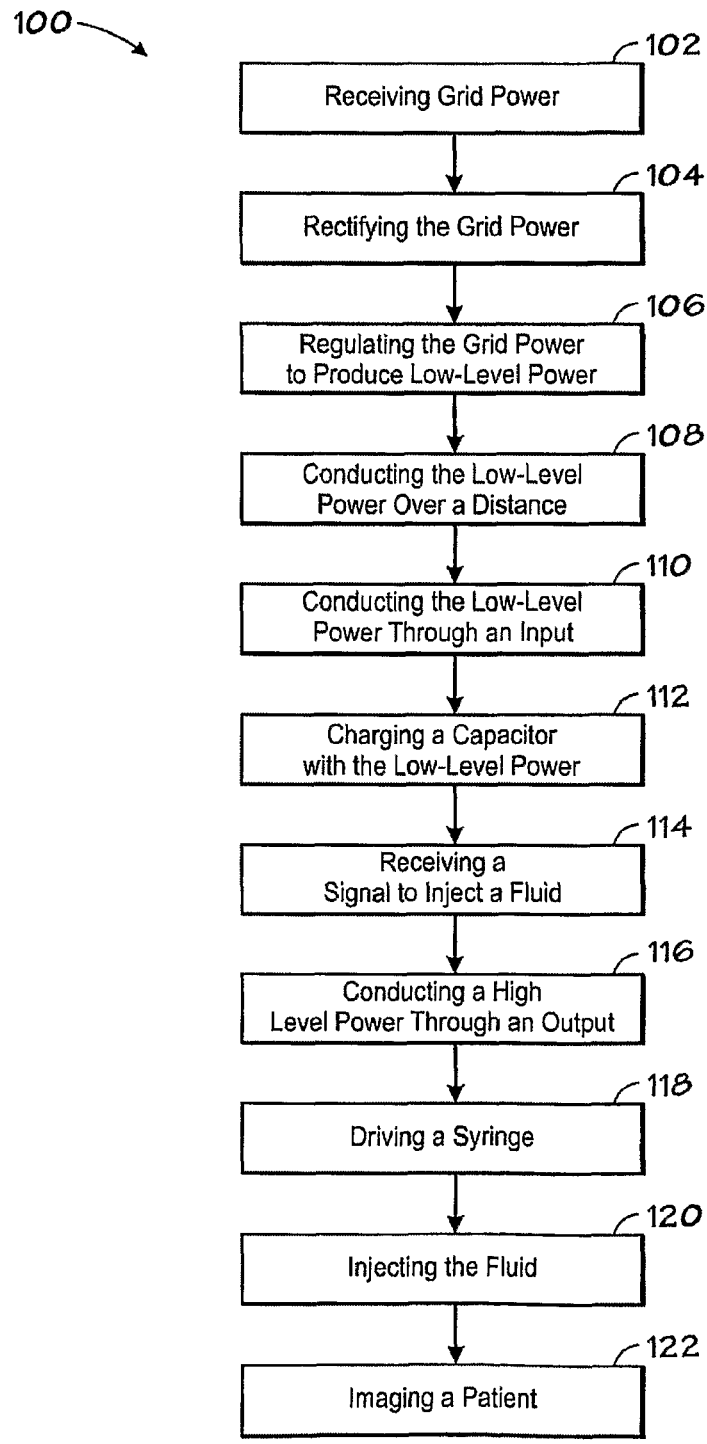
FIG. 5 is a flow chart depicting another exemplary injection process.

FIG. 5 depicts another exemplary injection process 100 that may be performed by the injection system 10 of FIGS. 1-3. The injection process 100 begins with receiving power from a power grid 22, as depicted by block 102, and, then, rectifying the power from the grid 22, as depicted by block 104. As an example, the rectifier 20 in the embodiment of FIG. 1 may rectify the power from the grid 22. Next, in the present embodiment, the power regulator 18 regulates the rectified power to produce low-level power, as depicted by block 106. The power cable 16 conducts the low-level power over a distance, such as between rooms 40, 42, as depicted by block 108.

The powered injector 12 may store and expend the energy delivered via the power cable 16. In the present embodiment, the low-level power may be conducted through an input 50 of the energy storage device 26, as depicted by block 110 of FIG. 5, and a capacitor 44 may be charged by a current carrying the low-level power, as depicted by block 112 of FIG. 5. Next, the controller 28 of the present embodiment may receive a signal to inject a fluid, as depicted by block 114 of FIG. 5. For instance, a user may press a button to initiate injection, and the button may transmit a signal to the controller 28. At this point, in some embodiments, the controller 28 may verify that the energy storage device 26 has stored sufficient energy to proceed with the injection. After the energy storage device 26 is partially charged, charged above a threshold value, or fully charged, the controller 28 may close a path through conductor 48 to conduct high-level power through output 46 of the energy storage device 26, as depicted by block 116 of FIG. 5. The motor 30 may receive the high-level power and drive the plunger of the syringe 34 via the ram 32, as depicted by block 118 of FIG. 5. As a result, medical fluid is expelled from the syringe 34 (e.g., injected into the patient 36), as depicted by block 120 of FIG. 5. Finally, in some embodiments, the patient 36 may be imaged, as depicted by block 122 of FIG. 5, for instance, with one of the imaging systems discussed in reference to imaging device 38 in FIG. 1.

Figure 6:
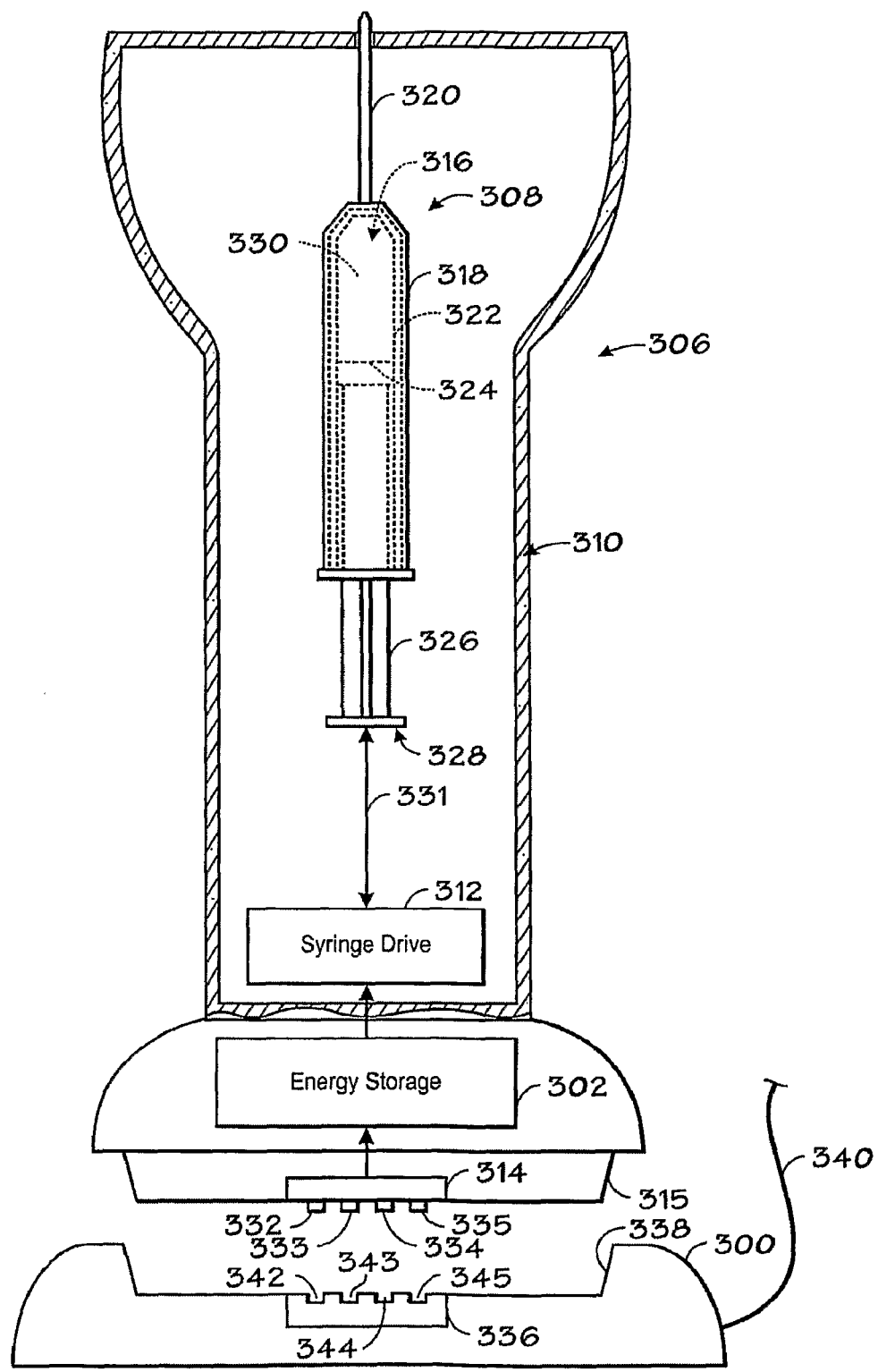
FIG. 6 is a cross-sectional view of an exemplary powered injector.

FIG. 6 illustrates an exemplary cordless injector 306 having an energy storage device 302 capable of being coupled to a docking station 300. As used herein, the term "cordless" refers to the capacity to operate without an external connection to a source of electrical power. The injector 306 may include one or more of the features of the previously discussed powered injector 12. The injector 306 features a shielded syringe assembly 308, shielding 310, a syringe drive 312, a docking station electrical interface 314, and a docking station mechanical interface 315. The docking station electrical interface 314 includes a plurality of leads 332, 333, 334, 335. These leads and/or others may be utilized in charging the injector 306 and/or as a communication link to enable the injector to communicate data to and/or through the docking station 300. In some embodiments, the injector 306 may be able to communicate data to and/or through the docking station 300 (e.g., to be conveyed to an imaging system and/or a hospital information system) via wireless communication (e.g., radio frequency).

In the present embodiment, syringe assembly 308 includes a syringe 316 and shielding 318. The illustrated syringe 316 includes a needle 320, a barrel 322, a plunger 324, and a push rod 326 having an outer end 328. One or more fluids 330 may be disposed within the barrel 322 of the syringe 316. For example, the fluid 330 may include a radiopharmaceutical, a contrast agent, saline, a pharmaceutical, or a combination thereof. The syringe 316 may exhibit any of a number of appropriate designs/configurations. For instance, in some embodiments, the syringe 316 may be a single stage syringe, a two stage syringe with different fluids in each stage, a multi-barrel syringe, or a syringe having more than two stages and/or more than two fluids.

The shielding 310, 318 of the injector 306 may include electromagnetic shielding, radiation shielding, thermal shielding, or some combination thereof. In some embodiments, the shielding 310, 318 may feature radiation shielding materials, such as lead, depleted uranium, tungsten, tungsten impregnated plastic, etc. Alternatively or additionally, shielding 310, 318 may include electromagnetic shielding materials, such as a layer, mesh, or other form of copper, steel, conductive plastic, or other conductive materials. In certain embodiments, the shielding 310, 318 may be substantially or entirely nonferrous. The shielding 310 may entirely envelope the syringe 316, the syringe drive 312, and/or the energy storage device 302; substantially envelope one or more of these components 316, 312, 302; or partially envelope one or more of these components 316, 312, 302. Similarly, the shielding 318 may entirely, substantially, or partially envelope the syringe 316. Some embodiments of the injector 302 may not include shielding 310 and/or 318, which is not to suggest that any other feature discussed herein may not also be omitted.

The syringe drive 312 of the injector 306 may include a piezoelectric drive, a linear motor, a shape memory alloy, a rack-and-pinion system, a worm gear and wheel assembly, a planetary gear assembly, a belt drive, a gear drive, a manual drive, a hydraulic drive, and/or a pneumatic drive. For example, in the embodiment of FIG. 8, discussed below, the syringe drive 312 may include an electric motor and a screw drive. In some embodiments, the syringe drive 312 may be entirely, substantially, or partially non-ferrous.

The docking station 300 for the injector 306 includes a complementary electrical interface 336, a complementary mechanical interface 338, and a power cable 340. The complementary electrical interface 336 includes a plurality of female connectors 342, 343, 344, 345. The power cable 340 may be adapted to receive power from a power source, such as a low wattage DC power source. Moreover, the docking station 300 may be mounted on a movable stand, a rotatable arm, a vehicle (e.g., ambulance), an imaging device, a patient table, a wall mount, or another suitable mount.

In operation, the cordless injector 306 is complementarily designed to mate with the docking station 300. Specifically, the docking station mechanical interface 315 of the injector 306 is designed to mate with the complementary mechanical interface 338 of the docking station 300, and the docking station electrical interface 314 of the injector 306 is designed to mate with the complementary electric interface 336 of the docking station 300. Energy flows through the power cable 340, through the female connectors 342, 343, 344, 345, and into the male connectors 332, 333, 334, 335 at low power. The low power energy flows into the energy storage device 302. In some embodiments, the energy storage device 302 may be charged while the injector is being utilized in a syringe filling procedure. For instance, while the energy storage device 302 is charging, the syringe drive 312 may apply force 331 that draws the plunger 324 away from the needle 320 within the barrel 322, thereby tending to pull fluid into the barrel 322. During filling, in situ or ex situ feed-forward or feed-back control may be exercised over the fill rate and/or fill volume.

When the energy storage device 302 is charged or energized, the cordless injector 306 may be removed from the docking station 300 and used to inject a radiopharmaceutical 330 or other appropriate medical fluid without power cables interfering with the procedure. Injection may be performed at the same site at which the cordless injector 306 is filled and charged, or the cordless injector 306 may be shipped in a charged and filled state for use at another site. During injection, energy may flow at a high rate from the energy storage device 302 to the syringe drive 312, which applies force 331 to the outer end 328 of the push rod 326. The push rod 326 drives the plunger 324 through the barrel 332 toward the needle 320 and, thus, causes the fluid 330 to be expelled from the syringe 316. During expulsion (e.g., injection) of the fluid 330, in situ or ex situ feed-forward or feed-back control may be exercised over the rate and/or volume of injection.

Figure 7:
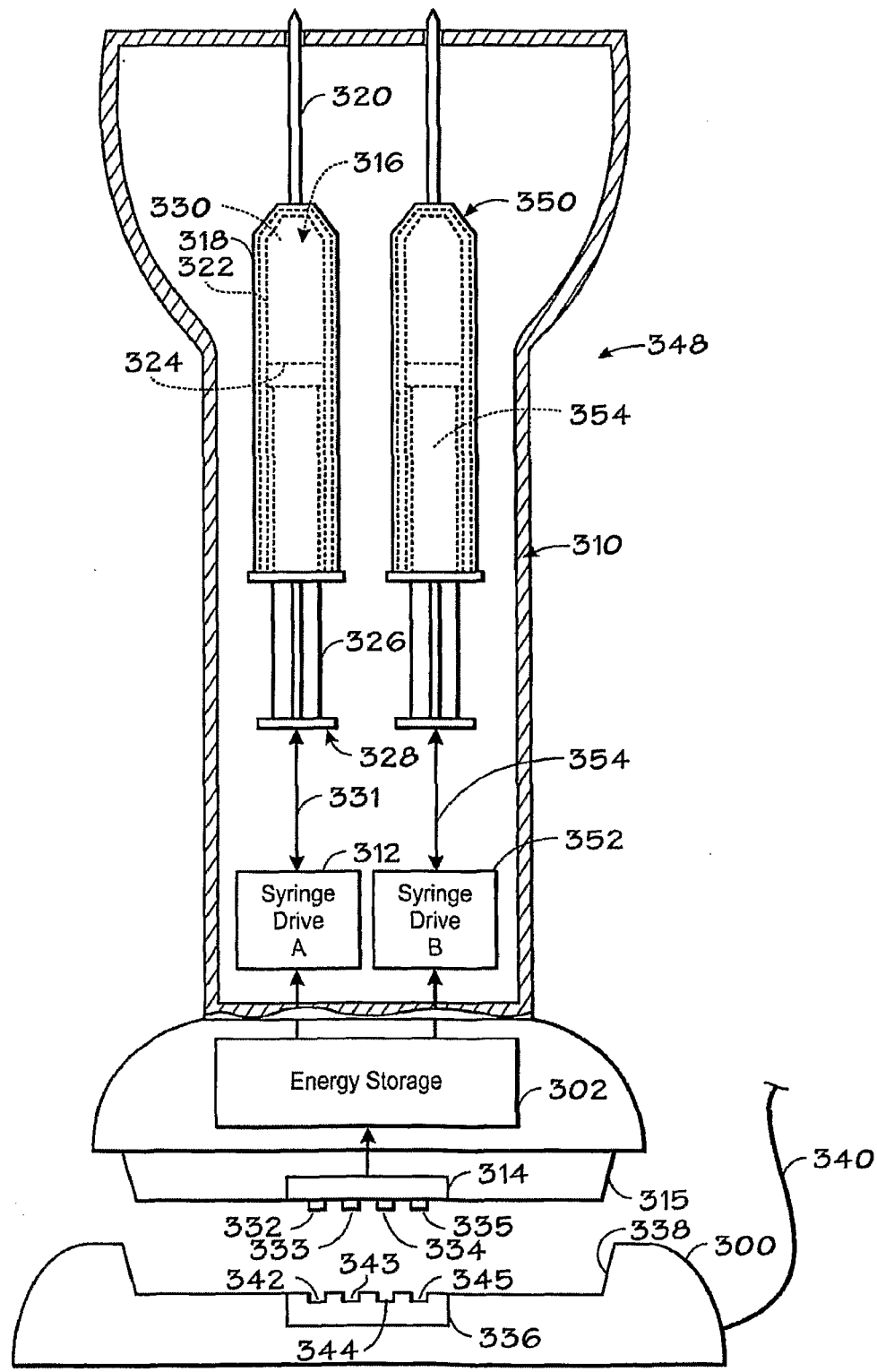
FIG. 7 is a cross-sectional view of an exemplary dual-syringe injector.

FIG. 7 illustrates an exemplary cordless injector 348 capable of accommodating a plurality of (here, two) syringes. The cordless injector 348 includes a secondary syringe 350 and a secondary syringe drive 352. The secondary syringe 350 may be shielded and may include fluid 354, which may be one or more of the medical fluids mentioned herein. The secondary syringe 350 may be within shielding 310, but in other embodiments, the secondary syringe 350 may be partially or entirely external to shielding 310. While the syringes shown in FIG. 7 are illustrated as being separate and distinct from one another, other embodiments of the injector 348 a capable of accommodating multi-barrel syringe assemblies (e.g., a substantially unitary, two-barreled syringe assembly).

In operation, the syringe drive 352 of the injector 348 may apply a force 354 to the plunger of the secondary syringe 350 and cause the fluid 354 to be drawn into or pushed out of the secondary syringe 350. In some embodiments, syringe drive 312 and secondary syringe drive 352 may be partially or entirely integrated into a single syringe drive. Alternatively, the syringe drive 312 and the secondary syringe drive 352 may be independent syringe drives. During injecting and/or filling, independent, in situ or ex situ feed-forward or feed-back control over the flow rate and/or volume of fluids 330 and/or 354 injected or filled by the cordless injector 348 may be exercised.

Figure 8:
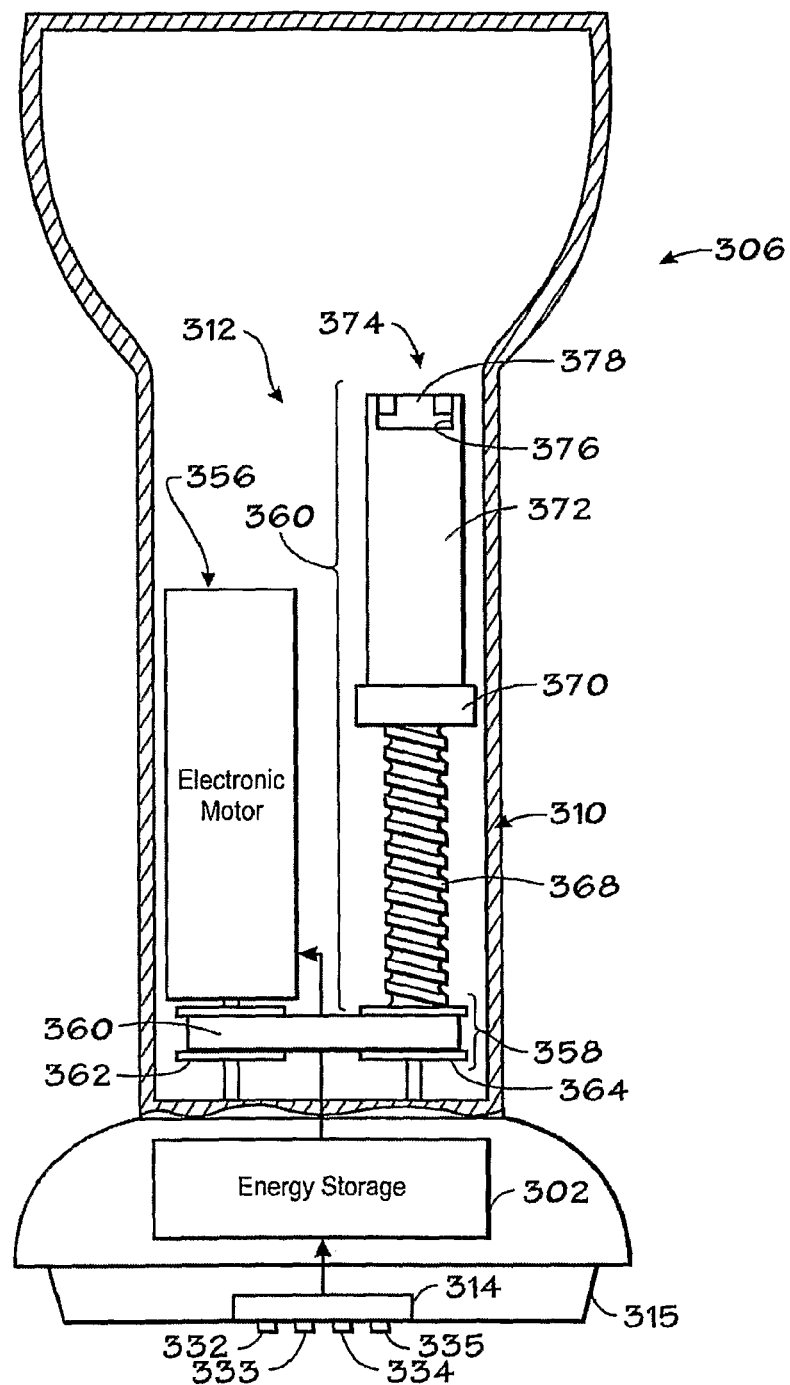
FIG. 8 is a cross-sectional view of an exemplary motor and ram for a powered injector.

FIG. 8 illustrates an exemplary syringe drive 312 within the cordless injector 306. The illustrated syringe drive 312 includes an electric motor 356, a transmission 358, and a linear drive 360. The electric motor 356 may be a DC electric motor or an AC electric motor, such as a stepper motor. The illustrated transmission 358 includes a primary pulley 362, a secondary pulley 364, and a belt 366. The present linear drive 360 has an externally threaded shaft, worm, or screw 368, a bushing 370, an outer shaft 372, and a syringe interface 374. The transmission 358 may have a ratio of the diameter of the secondary pulley 364 to the diameter of the primary pulley 362 of greater than 0.5:1, greater than 1.0:1, greater than 1.5:1, greater than 2:1, greater than 3:1, greater than 4:1, greater than 5:1, greater than 8:1, greater than 20:1, or more. The syringe interface 374 includes a wider, outer-end receptacle 376 and a shaft slot 378. In some embodiments, one or more of the motor 356, transmission 358, and drive 360 may be substantially or entirely non-ferrous. In some embodiments, one or more of the motor 356, transmission 358, and drive 360 may be partially, substantially, or entirely shielded by shielding 310.

In operation, the electric motor 356 of the injector 306 drives the primary pulley 362. As the primary pulley 362 rotates, the belt 366 rotates the secondary pulley 364. The rotation of the secondary pulley 364 drives the screw 368, which rotates within the bushing 370. The bushing 370 is threaded so that rotation of the screw 368 applies a linear force to the bushing 370. A linear sliding mechanism may prevent rotation of the bushing 370 while permitting the bushing 370 to translate up and down the screw 368. As the screw 368 rotates, the outer shaft 372 may be pulled down the screw 368 or pushed up the screw 368 by the bushing 370. The outer shaft 372 may linearly translate relative to the screw 368 and move the plunger of the syringe 316 via the syringe interface 374.

While the invention may be susceptible to various modifications and alternative forms, specific embodiments have been shown by way of example in the figures and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A powered injector for injecting medical fluid, the powered injector comprising:
   a single, on-board energy storage device that comprises:
      a power input having an input current carrying capacity; and
      a power output having an output current carrying capacity, wherein the output current carrying capacity is greater than the input current carrying capacity such that the power input is at a low rate and the power output is at a high rate;
   a motor coupled to the power output of the single, on-board energy storage device; and
   a ram coupled to the motor and having a syringe plunger interface.

2. The powered injector of claim 1, wherein the single, on-board energy storage device comprises one or more capacitors.

3. The powered injector of claim 2, wherein the one or more capacitors have a series capacitance greater than about 30 farads.

4. The powered injector of claim 2, wherein the one or more capacitors comprises a series of serially connected supercapacitors, wherein one end of the series of supercapacitors is coupled to the input of the single, on-board energy storage device, and wherein another end of the series of supercapacitors is coupled to the output of the single, on-board energy storage device.

5. The powered injector of claim 1, further comprising:
a power cable connected to the input of the single, on-board energy storage device; and
a power source external to the powered injector and connected to the input of the single, on-board energy storage device via the power cable.

6. The powered injector of claim 5, wherein a substantial portion of a length of the power cable consists essentially of insulated wire having a conductive portion with a cross-sectional area of less than about $2.6 \times 10^{-3}$ square inch.

7. The powered injector of claim 5, wherein the single, on-board energy storage device is coupled to the power source via both the power cable and protection circuitry.

8. The powered injector of claim 5, wherein the power source is a power source of less than about 500 watts.

9. The powered injector of claim 6, wherein the single, on-board energy storage device is configured to output more than about 1000 watts of power when the single, on-board energy storage device is in an energized state.

10. The powered injector of claim 1, further comprising:
a syringe having a medical fluid therein, wherein the syringe is coupled to the syringe plunger interface of the ram.

11. The powered injector of claim 1, wherein the power input is the only power input into the single, on-board energy storage device.

12. An electric injector for use with a syringe having medical fluid therein, the injector comprising:
a single, on-board energy storage device comprising a plurality of supercapacitors coupled to one another in series;
a motor coupled in parallel to the plurality of supercapacitors; and
a syringe interface coupled to the motor.

13. The injector of claim 12, wherein the plurality of supercapacitors have a combined capacitance greater than about one thousand farads.

14. The injector of claim 12, wherein the plurality of supercapacitors comprises more than four supercapacitors.

15. The injector of claim 12, further comprising:
a conductor having a current carrying capacity greater than about 10 amps, wherein the motor is connected to the plurality of supercapacitors through the conductor.

16. The injector of claim 12, further comprising:
a controller having a switch configured to transmit more than about 800 watts of power when in a closed state, wherein the switch is disposed in series between the plurality of supercapacitors and the motor.

17. A method of medical fluid injector operation, the method comprising:
receiving energy from a remote power supply at an input wattage;
storing the energy on board the medical fluid injector; and
outputting at least a portion of the energy to a motor at an output wattage, wherein the output wattage is at least twice as great as the input wattage.

18. The method of claim 17, wherein the storing comprises charging a bank of capacitors having a capacitance greater than about 1 farad.

19. The method of claim 17, wherein the output wattage is greater than about 500 watts.

20. The method of claim 17, wherein the outputting comprises moving a ram of the injector.

* * * * *